United States Patent [19]

Griffiths et al.

[11] Patent Number: 5,200,527

[45] Date of Patent: Apr. 6, 1993

[54] PROCESS FOR THE PRODUCTION OF 2-AZABICYCLO [2.2.1] HEPT-5-EN-3-ONE

[75] Inventors: Gareth Griffiths, Visp; Felix Previdoli, Brig, both of Switzerland

[73] Assignee: Lonza Ltd., Gampel/Valais, Switzerland

[21] Appl. No.: 863,683

[22] Filed: Apr. 1, 1992

[30] Foreign Application Priority Data

Apr. 8, 1991 [CH] Switzerland ............... 1034/91

[51] Int. Cl.$^5$ ........................... C07D 209/52
[52] U.S. Cl. ..................... 548/452; 548/543; 548/552; 548/553
[58] Field of Search ................ 548/512, 452

[56] References Cited

U.S. PATENT DOCUMENTS 4,118,393 10/1978 Faushawe et al. .............. 548/512

OTHER PUBLICATIONS

Chemical Abstracts, vol. 111, No. 5, Jul. 31, 1989), Abstract No. 111: 39161p.
J. C. Jagt and A. M. van Larsen, J. Org. Chem., vol. 39, (1974), pp. 564 to 566.
S. Daluge and R. Vince, vol. 43, No. 12, (Jun. 9, 1978), pp. 2311 to 2320).
J. R. Malpass and N. J. Tweddle, vol. 1977, No. 8, (1977), J. Chem. Soc., Perkin I, pp. 874 to 884.
M. S. A. Vrijland, Org. Synth., Coll. vol. VI, pp. 727 to 730 (1970).

Primary Examiner—David B. Springer
Attorney, Agent, or Firm—Fisher, Christen & Sabol

[57] ABSTRACT

2-Azabicyclo[2.2.1]hept-5-en-3-one is produced by Diels-Alder reaction of cyclopentadiene and methanesulfonyl cyanide and then hydrolytic cleavage of the methanesulfonyl group.

12 Claims, No Drawings

PROCESS FOR THE PRODUCTION OF 2-AZABICYCLO [2.2.1] HEPT-5-EN-3-ONE

BACKGROUND OF THE INVENTION

1. Field Of The Invention

The invention relates to a process for the production of (±)-2-azabicyclo[2.2.1]hept-5-en-3-one having the formula:

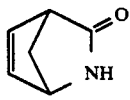

2. Background Art

2-Azabicyclo[2.2.1]hept-5-en-3-one is a bicyclic lactam which is suitable as starting material for the synthesis of carboxylic nucleoside analogues [S. Daluge and R. Vince, J. Org. Chem., Vol. 43, (1978), page 2311]. Such nucleoside analogues are of interest because of their antiviral and chemotherapeutic properties as potential anti-tumor agents. A known synthesis of 2-azabicyclo[2.2.1]hept-5-en-3-one starts from 1,3-cyclopentadiene, which forms with chlorosulfonylisocyanate in a 1,2 addition a bicyclic N-chlorosulfonyl-β-lactam, which is rearranged in the corresponding 1,4 addition product and provides the target compound by hydrolytic cleavage of the N-chlorosulfonyl group in poor yield (27.5 percent) [J. R. Malpass and N. J. Tweddle, J. Chem. Soc. Perkin I, (1977), page 874].

Another known synthesis is based on the Diels-Alder reaction of cyclopentadiene with p-toluenesulfonyl cyanide. In this case, a tosyl-azanorbornadiene results first, which is converted by acid or alkaline hydrolysis into the target compound [J. C. Jagt and A. M. van Larsen, J. Org. Chem., Vol. 39, (1974), page 564,; S. Daluge and R. Vince, loc. cit.]. Drawbacks of this process are the explosiveness of p-toluenesulfonyl cyanide and the unfavorable quantitative ratio of the product to the by-product p-tolylsulfinyl-p-tolylsulfone. Moreover, the cyclopentadiene is used in great excess which has to be distilled off prior to the hydrolysis.

BROAD DESCRIPTION OF THE INVENTION

The object of the invention was to provide a process for the production of 2-azabicyclo[2.2.1]hept-5-en-3-one, which, starting from favorably priced feedstock, yields the desired product to be produced in a simple way and in good yield without large amounts of waste. Other objects and advantages of the invention are set out herein or are obvious herefrom to one skilled in the art.

The objects and advantages of the invention are achieved by the process and intermediate product of the invention.

The invention involves a process for the production of 2-azabicyclo[2.2.1]hept-5-en-3-one. 1,3-Cyclopentadiene is reacted with methanesulfonyl cyanide in a Diels-Alder reaction to 3-methanesulfonyl-2-azabicyclo[2.2.1]hepta-2,5-diene and then the latter is hydrolyzed to 2-azabicyclo[2.2.1]hept-5-en-3-one.

Preferably the hydrolysis is performed in the presence of an acid. Preferably carboxylic acid is used as the acid, and preferably acetic acid is used as the carboxylic acid. Preferably the Diels-Alder reaction is performed in a solvent at a temperature of −50° to +100° C. Preferably the Diels-Alder reaction is performed at a temperature of −20° to +40° C. Preferably the solvent is a halogenated aliphatic or aromatic hydrocarbon, a aromatic hydrocarbon, or a acyclic or cyclic ether. Preferably dichloromethane is used as the solvent. Preferably the 3-methanesulfonyl-2-azabicyclo[2.2.1]hepta-2,5-diene is hydrolyzed without previously being isolated.

The invention also includes (±)-3-methanesulfonyl-2-azabicyclo[2.2.1]hepta-2,5-diene.

DETAILED DESCRIPTION OF THE INVENTION

It was found that cyclopentadiene in stoichiometric amounts or in slight excess can react smoothly with methanesulfonyl cyanide to the corresponding Diels-Alder adduct 3-methanesulfonyl-2-azabicyclo[2.2.1]hepta-2,5-diene, having the formula:

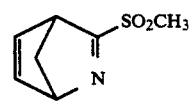

which can be hydrolyzed easily to 2-azabicyclo[2.2.1]hept-5-en-3-one. Methanesulfonyl cyanide can be produced according to a known processss from methanesulfonyl chloride or sodium methanesulfonate [M. S. A. Vrijland, Org. Synth., Coll. Vol. VI, pages 727 to 730].

The hydrolysis of the Diels-Alder adduct can be performed both under acid and base catalysis, preferably an acid is used as the catalyst. Especially preferred are carboxylic acids, such as, lower aliphatic carboxylic acids, especialiy acetic acid.

The Diels-Alder reaction is performed preferably in a solvent at a temperature of −50° to +100° C. A reaction temperature of −20° to +40° C. is especially preferred. As the solvent basically all solvents are suitable which do not themselves react with one of the reactants or the Diels-Alder adduct. Preferably the solvent is used from the group of halogenated aliphatic or aromatic hydrocarbons, such as, dichloromethane, 1,2-dichloroethane and chlorobenzene, of the aromatic hydrocarbons, such as, benzene, toluene and xylene, and of the acyclic and cyclic ethers, such as, diethyl ether, diisopropyl ether, methyl-tert-butyl ether and tetrahydrofuran. Especially preferred is dichloromethane. The cyclopentadiene itself can be used as the solvent, by using it in excess.

The Diels-Alder adduct 3-methanesulfonyl-2-azabicyclo[2,2.1]hepta-2,5-diene can be isolated in the usual way and optionally be mildly purified, but because of its low stability, it is preferably subjected directly to hydrolysis without isolation.

The following examples illustrate the performance of the process according to the invention.

EXAMPLE 1

(±)-3-Methanesulfonyl-2-azabicyclo[2.2.1]hepta-2,5-diene 7.93 g of cyclopentadiene (120 mmol) was added to a solution of 10.51 g of methanesulfonyl cyanide (100 mmol) in 30 ml of dichloromethane within 5 minutes at −20° C. The colorless solution was stirred for another 2 hours at room temperature and then the solvent was distilled off, and the Diels-Alder adduct remains as yellowish solid. Properties of the compound were:

| | |
|---|---|
| Melting point: 52° to 53° C. | |
| $^1$H-NMR (CDCl$_3$, 300 MHz): δ | 2.10(d, J=8Hz, 1H) |
| | 2.28(d, J=8Hz, 1H) |
| | 3.15(s, 3H) |
| | 4.45(m, 1H) |
| | 5.47(m, 1H) |
| | 6.89(m, 2H) |

EXAMPLE 2

(±)-2-Azabicyclo[2.2.1]hept-5-en-3-one

A solution of 2.55 g of cyclopentadiene (38.6 mmol) in 10 ml of dichloromethane cooled to −20° C. was added to a solution of 3.61 g of methanesulfonyl cyanide (97 percent, 33.3 mmol) in 30 ml of dichloromethane within 5 minutes. In this connection the reaction temperature fluctuated between 17° and 22° C. The colorless solution was stirred for another 2 hours at room temperature and then mixed with 6 ml of acetic acid. 60 ml of water was added within 1 minute and the mixture was neutralized with 30 percent sodium hydroxide solution (pH≅8). The phases were separated and the aqueous phase was extracted three times each with 25 ml of dichloromethane. The combined organic phases were dried on MgSO$_4$, filtered and evaporated to dryness. The colorless solid residue was dried at 30° C./300 mbar. There was a yield of 2.54 g, corresponding to 70 percent of theory, relative to methanesulfonyl cyanide. The purity (GC) was about 100 percent. The product had a melting point of 50° to 53° C.

What is claimed is:

1. A process for the production of 2-azabicyclo[2.2.1]hept-5-en-3-one comprising: reacting 1,3-cyclopentadiene with methanesulfonyl cyanide in a Diels-Alder reaction in an inert solvent at a temperature of −50° to +100° C. to 3-methanesulfonyl-2-azabicyclo[2.2.1]hepta-2,5-diene; and then hydrolyzing the latter compound to 2-azabicyclo[2.2.1]hept-5-en-3-one.

2. The process according to claim 1 wherein the hydrolysis is performed in the presence of an acid.

3. The process according to claim 2 wherein a carboxylic acid is used as the acid.

4. The process according to claim 3 wherein acetic acid is used as the carboxylic acid.

5. The process according to claim 4 wherein the Diels-Alder reaction is performed at a temperature of −20° to +40° C.

6. The process according to claim 4 wherein the solvent is selected from the group of solvents consisting of a halogenated aliphatic hydrocarbon, a halogenated aromatic hydrocarbon, an aromatic hydrocarbon, an acyclic ether and a cyclic ether.

7. The process according to claim 6 wherein dichloromethane is used as the solvent.

8. The process according to claim 7 wherein 3-methanesulfonyl-2-azabicyclo[2.2.1]hepta-2,5-diene is hydrolyzed without previously being isolated.

9. The process according to claim 1 wherein the Diels-Alder reaction is performed at a temperature of −20° to +40° C.

10. The process according to claim 1 wherein the solvent is selected from the group of solvents consisting of a halogenated aliphatic hydrocarbon, a halogenated aromatic hydrocarbon, an aromatic hydrocarbon, an acyclic ether and a cyclic ether.

11. The process according to claim 1 wherein 3-methanesulfonyl-2-azabicyclo[2.2.1]hepta-2,5-diene is hydrolyzed without previously being isolated.

12. (±)-3-Methanesulfonyl-2-azabicyclo[2.2.1]hepta-2,5-diene.

* * * * *